US012077473B1

(12) United States Patent
Wang et al.

(10) Patent No.: US 12,077,473 B1
(45) Date of Patent: Sep. 3, 2024

(54) INORGANIC SOLID WASTE-MICROBIAL COMPOSITE CURING AGENT AND ITS PREPARATION METHOD AND APPLICATION

(71) Applicant: CHINA CONSTRUCTION INDUSTRIAL & ENERGY ENGINEERING GROUP CO., LTD., Nanjing (CN)

(72) Inventors: Anhui Wang, Nanjing (CN); Zhanwei Huang, Nanjing (CN); Yanfang Zhang, Nanjing (CN); Jiaojiao Ni, Nanjing (CN); Rui Zhang, Nanjing (CN); Jiao Lin, Nanjing (CN)

(73) Assignee: CHINA CONSTRUCTION INDUSTRIAL & ENERGY ENGINEERING GROUP CO., LTD.

( * ) Notice: Subject to any disclaimer, the term of this patent is extended or adjusted under 35 U.S.C. 154(b) by 0 days.

(21) Appl. No.: 18/603,602

(22) Filed: Mar. 13, 2024

(30) Foreign Application Priority Data

Mar. 14, 2023 (CN) ........................ 202310242854.X

(51) Int. Cl.

| | |
|---|---|
| ***C04B 20/02*** | (2006.01) |
| ***C04B 40/00*** | (2006.01) |
| ***C04B 40/02*** | (2006.01) |
| ***C04B 111/00*** | (2006.01) |
| ***C12N 1/20*** | (2006.01) |
| ***C12R 1/125*** | (2006.01) |

(52) U.S. Cl.
CPC ........ *C04B 20/023* (2013.01); *C04B 40/0042* (2013.01); *C04B 40/0231* (2013.01); *C12N 1/205* (2021.05); *C04B 2111/00767* (2013.01); *C12R 2001/125* (2021.05)

(58) Field of Classification Search
CPC .............. C04B 20/023; C04B 40/0042; C04B 40/0231; C04B 2111/00767; C12N 1/205; C12R 2001/125
See application file for complete search history.

(56) References Cited

FOREIGN PATENT DOCUMENTS

| | | | |
|---|---|---|---|
| CN | 110183194 | A | 8/2019 |
| CN | 110204289 | A | 9/2019 |
| CN | 111775270 | A | 10/2020 |
| CN | 113666705 | A | 11/2021 |
| CN | 114751702 | A | 7/2022 |
| JP | 2005335969 | A | 12/2005 |
| KR | 20200101023 | A | 8/2020 |
| WO | 2022000524 | A1 | 1/2022 |

OTHER PUBLICATIONS

First Examination Report and Search Report of CNIPA, Jan. 11, 2024.

Notice of Allowance from CNIPA and Allowed Claims, Feb. 21, 2024.

Yang Yi fan , et al. "A Study on Engineering Characteristics of Stabilized-Soil Made From Recycled Powder-Slag Without Clinker" Mining And Metallurgy, Oct. 25, 2016.

*Primary Examiner* — Anthony J Green

(57) ABSTRACT

Provided is an inorganic solid waste-microbial composite curing agent and its preparation method and application. The inorganic solid waste-microbial composite curing agent consists of the following raw materials in parts by weight: steel slag, active magnesium oxide, recycled powder, stearic acid, borax, carbonic anhydrase bacteria, *Bacillus subtilis*, and soluble calcium salts. The preparation method includes performing granulation on steel slag, active magnesium oxide, recycled powder, stearic acid, borax, etc. into porous materials through dry rolling extrusion and compression, and loading carbonic anhydrase bacteria and *Bacillus subtilis* into the porous materials. By adding inorganic solid waste-microbial composite curing agent into the sludge and introducing $CO_2$, the sludge is quickly solidified through the carbonization and microbial mineralization of inorganic solid waste. At the same time, microorganisms can effectively decompose organic pollutants in the sludge, achieving the goal of harmless, stabilized and resourceful utilization of sludge.

7 Claims, No Drawings

INORGANIC SOLID WASTE-MICROBIAL COMPOSITE CURING AGENT AND ITS PREPARATION METHOD AND APPLICATION

CROSS-REFERENCE

This application claims to the benefit of priority from Chinese Application No. 202310242854.X with a filing date of Mar. 14, 2023. The content of the aforementioned applications, including any intervening amendments thereto, are incorporated herein by reference.

TECHNICAL FIELD

The present disclosure relates to the technical field of curing agent, in particular to an inorganic solid waste-microbial composite curing agent and its preparation method and application.

BACKGROUND

With the rapid development of economy and urbanization construction in China, infrastructure construction has entered an accelerated period. During the construction process, engineering waste soil is often encountered, such as construction waste sludge. Construction waste sludge is generally treated by landfill or stacking, which takes up a large amount of land resources and poses a serious threat to the ecological environment. Construction waste sludge has high compressibility, high moisture content, poor permeability, high clay content, slow drainage consolidation, and low bearing capacity, making it difficult to directly use as a building material in engineering. It is necessary to use curing agents to solidify the sludge, convert it into good building materials, so as to solve the problems of environmental pollution and land occupation caused by construction waste sludge.

Cement is currently the most commonly used sludge curing agent. However, there are still some insurmountable shortcomings in the production and application of cement. Firstly, cement requires a large amount of resources and energy consumption in the production process, such as limestone, clay, and standard coal. Secondly, the cement production process will emit a large amount of harmful waste gases such as $CO_2$, dust, $SO_2$, CO, $NO_x$, etc., which will cause serious pollution to the ecological environment. At the same time, there are a large amount of organic matter and other pollutants in the sludge, which can inhibit the hydration reaction of cement. In practical use, it is necessary to increase the cement content to improve the strength of the solidified sludge. However, excessive cement content can significantly increase the pH value of the leaching solution, which is not conducive to the stability of certain pollutants and can also have adverse effects on groundwater and surrounding vegetation. The use of microbial mineralization to reinforce soil can improve its strength and stiffness. Compared with traditional curing agents, microbial curing agents have the characteristics of low energy consumption, low pollution, and low emissions. However, the growth and activity of microorganisms are greatly affected by the surrounding environment. Therefore, when using microbial mineralization to reinforce soil, the curing efficiency is lower, leading to lower strength of solidified soil.

In summary, in order to solve the above problems, achieve energy conservation and emission reduction, and improve the strength of sludge solidification, the present disclosure provides an inorganic solid waste-microbial composite curing agent and its preparation method and application.

SUMMARY

The objective of the present disclosure is to provide an inorganic solid waste-microbial composite curing agent and its preparation method and application, in order to solve the problems proposed in the background technology.

In order to solve the above-mentioned technical problems, the present disclosure provides the following technical solutions:

An inorganic solid waste-microbial composite curing agent includes the following components in parts by weight: 20-30 parts of steel slag, 30-40 parts of activated magnesium oxide, 20-30 parts of recycled powder, 5-10 parts of foaming agent, 1-5 parts of foam stabilizer, 0.4-0.8 parts of composite microbial agent, 2-8 parts of soluble calcium salt; the composite microbial agent includes carbonic anhydrase bacteria microcapsules, *Bacillus subtilis* microcapsules.

As further improvement, the recycled powder is construction waste powder; the foaming agent is stearic acid; and the foam stabilizer is borax.

As further improvement, the steel slag, the activated magnesium oxide, the recycled powder, the foaming agent, the foam stabilizer are sieved through a 100 mesh sieve.

As further improvement, the soluble calcium salt is any one of calcium chloride, calcium bromide, calcium nitrate, and calcium bicarbonate.

A method of preparing the inorganic solid waste-microbial composite curing agent, including the following steps:

S1. Preparation of Solid Waste Porous Material mixing the steel slag, the activated magnesium oxide, the recycled powder, the foaming agent, the foam stabilizer and performing extrusion granulation, heating the material to 1110-1120° C., then cutting, granulating, and sieving to obtain a solid waste porous material;

S2. Modification of the Solid Waste Porous Material taking zinc nitrate hexahydrate and ferrous chloride to add into a mixed solution of methanol and deionized water, then adding the solid waste porous material, stirring for 2-3 h, then washing and drying to obtain a modified solid waste porous material;

S3. Cultivation of Carbonic Anhydrase Bacteria and *Bacillus subtilis* with High pH Resistance conducting domestication on carbonic anhydrase bacteria and *Bacillus subtilis* separately, while adjusting a pH of a culture solution to 10-12, and screening the carbonic anhydrase bacteria and the *Bacillus subtilis* to obtain the carbonic anhydrase bacteria and *Bacillus subtilis* that are able to tolerate a pH of 10;

S4. Preparation of the Composite Bacterial Agent of Carbonic Anhydrase Bacteria and *Bacillus subtilis* performing centrifugation to obtain carbonic anhydrase bacterial sludge and *Bacillus subtilis* bacterial sludge respectively, then separately adding sodium alginate saturated solution, then performing centrifugation after stirring to obtain carbonic anhydrase bacteria microcapsules and *Bacillus subtilis* microcapsules, respectively, then mixing the carbonic anhydrase bacteria microcapsules and the *Bacillus subtilis* microcapsules uniformly, and then drying to obtain the composite microbial agent;

S5. Preparation of the Inorganic Solid Waste-Microbial Composite Curing Agent adding the composite microbial agent and the soluble calcium salt into deionized water to obtain a mixed solution, then impregnating the modified solid waste porous material in the mixed solution for 15-20 min under vacuum negative pressure, then drying to obtain the inorganic solid waste-microbial composite curing agent.

As further improvement, the mass ratio of the carbonic anhydrase bacteria microcapsules, *Bacillus subtilis* microcapsules is (1-2):(1-2).

An application of an inorganic solid waste-microbial composite curing agent includes the following steps:

step 1: crushing and sieving the inorganic solid waste-microbial composite curing agent to obtain an inorganic solid waste-microbial composite curing agent A with a particle size of 0.17-3 mm and an inorganic solid waste-microbial composite curing agent B with a particle size of 0.075-0.16 mm;

step 2: spraying a 5-8% calcium chloride solution onto surfaces of the inorganic solid waste-microbial composite curing agent A and the inorganic solid waste-microbial composite curing agent B to keep the surfaces wet, spraying at intervals of 6-8 hours once, and repeating 2-3 times;

step 3: mixing and stirring the inorganic solid waste-microbial composite curing agent B and the sludge for 5-10 min;

step 4: adding the inorganic solid waste-microbial composite curing agent A, and continuously stirring for 5-10 min;

step 5: moulding a specimen after standing for 10-12 h, placing the specimen into a sealed space, then introducing $CO_2$ to conduct carbonisation, demoulding the specimen after 48 hours, and then curing for the specimen to obtain an ecological porous building material.

As further improvement, in the step 3, the mass ratio of the inorganic solid waste-microbial composite curing agent B and the sludge is 1:(5-10), and the moisture content of the sludge is 40%-60%;

in the step 4, the inorganic solid waste-microbial composite curing agent A accounts for 30%-40% of the mass of the sludge;

in the step 5, the curing temperature is 18-25° C., and the humidity is 95-98 percent.

Compared with the related arts, the advantageous effects achieved by the present disclosure are shown as following:

(1) The present disclosure provides an inorganic solid waste-microbial composite curing agent and its preparation method and application, which not only solves the shortcomings of traditional curing agents such as high energy consumption and high pollution emissions, but also overcomes the problem of low curing efficiency of microbial curing agents. In addition, the composite curing agent of the present disclosure can store and absorb a large amount of $CO_2$ during the curing process of sludge, saving energy and reducing emissions, and has good economic benefits and engineering application prospects.

The microorganisms added in the present disclosure are carbonic anhydrase bacteria and *Bacillus subtilis*. Carbonic anhydrase bacteria can convert $CO_2$ into $CO_3^{2-}$, and *Bacillus subtilis* can effectively decompose organic pollutants in sludge.

The present disclosure uses a granulator to perform dry rolling extrusion granulation on steel slag, active magnesium oxide, recycled powder, stearic acid, and borax into solid waste porous materials. Carbonic anhydrase bacteria and *Bacillus subtilis* are encapsulated in microcapsules and loaded into the solid waste porous materials to effectively protect microorganisms. In engineering applications, the inorganic solid waste-microbial composite curing agent is added to the sludge, and $CO_2$ is introduced during the curing process. On the one hand, $CO_2$ can provide a carbon source for carbonic anhydrase bacteria, promote microbial mineralization, on the other hand, it can react with $Ca^{2+}$ in inorganic solid waste to form $CaCO_3$ through microbial mineralization and the carbonization of inorganic solid waste, so that the sludge can be quickly solidified. At the same time, microorganisms can effectively decompose organic pollutants in the sludge, to achieve the goal of harmless, stable, and resource utilization of sludge. In addition, the curing process of sludge can absorb a large amount of greenhouse gas $CO_2$, achieving energy conservation and emission reduction, which is beneficial for ecological environment protection.

(3) By using sodium alginate as the wall material, and using carbonic anhydrase bacteria and *Bacillus subtilis* as the core material, the present disclosure prepares microcapsules of carbonic anhydrase bacteria and *Bacillus subtilis*.

Solid waste porous materials are immersed in solutions such as zinc nitrate hexahydrate and ferrous chloride, causing iron ions and zinc ions to be carried inside the solid waste porous materials. By compounding solid waste porous materials and microcapsules, sodium alginate wall materials on microcapsules of carbonic anhydrase bacteria and *Bacillus subtilis* can chelate with iron ions and zinc ions, so as to tightly combining the two. At the same time, solid waste porous materials can provide good protection for microcapsules.

DETAILED DESCRIPTION OF THE EMBODIMENTS

The following will provide a clear and complete description of the technical solutions in the embodiments of the present disclosure. Obviously, the described embodiments are only a part of the embodiments of the present disclosure, not all of them. Based on the embodiments in the present disclosure, all other embodiments obtained by ordinary skilled person in the art without creative labor fall within the scope of the present disclosure.

Embodiment 1

A method of preparing the inorganic solid waste-microbial composite curing agent includes the following steps:

S1. Preparation of Solid Waste Porous Material

Performing granulation on steel slag, active magnesium oxide, recycled powder, stearic acid, borax through dry rolling extrusion and compression using a granulator, which can effectively maintain the mineral activity of the steel slag and recycled powder. The heating device is turned on to raise the temperature of the material to 1120° C., and the solid waste porous material with a diameter of 2-3 mm is obtained through cutting, granulating, and screening processes.

Solid waste porous materials, calculated by weight, include: 20 parts of the steel slag, 30 parts of the active magnesium oxide, 30 parts of the recycled powder, 5 parts of the stearic acid, and 1 part of the borax.

S2. Modification of the Solid Waste Porous Material

Taking zinc nitrate hexahydrate and ferrous chloride to add into a mixed solution of methanol and deionized water, then adding the solid waste porous material, stirring for 3 h, then washing and drying to obtain a modified solid waste porous material.

The mass ratio of the zinc nitrate hexahydrate, the ferrous chloride, the methanol, the deionized water, and the solid waste porous material is 12:3:200:300:500.

S3. Cultivation of Carbonic Anhydrase Bacteria and *Bacillus subtilis* with High pH Resistance Inoculating carbonic anhydrase bacteria and *Bacillus subtilis* into culture dishes with a pH value of 12, screening and domesticating them to obtain carbonic anhydrase bacteria and *Bacillus subtilis* that can tolerate pH 10;

S4. Preparation of the Composite Bacterial Agent of Carbonic Anhydrase Bacteria and *Bacillus subtilis*

Performing centrifugation to obtain carbonic anhydrase bacterial sludge and *Bacillus subtilis* bacterial sludge respectively, taking 1 weight part of the carbonic anhydrase bacterial sludge and adding it into 200 weight parts of sodium alginate saturated solution, then performing centrifugation after stirring to obtain carbonic anhydrase bacteria microcapsules; taking 1 weight part of the *Bacillus subtilis* bacterial sludge and adding it into 200 weight parts of sodium alginate saturated solution, then performing centrifugation after stirring to obtain *Bacillus subtilis* microcapsules;

Then mixing 0.2 weight parts of the carbonic anhydrase bacteria microcapsules and 0.2 weight parts of the *Bacillus subtilis* microcapsules uniformly, and then drying to obtain the composite microbial agent;

S5. Preparation of the Inorganic Solid Waste-Microbial Composite Curing Agent

Adding 0.4 weight parts of the composite microbial agent and 6 weight parts of the soluble calcium salt into 50 weight parts of deionized water to obtain a mixed solution, then impregnating the modified solid waste porous material obtained in S2 into the mixed solution for 20 min under vacuum negative pressure, then drying to obtain the inorganic solid waste-microbial composite curing agent.

Crushing and sieving the inorganic solid waste-microbial composite curing agent to obtain an inorganic solid waste-microbial composite curing agent A with a particle size of 0.17-3 mm and an inorganic solid waste-microbial composite curing agent B with a particle size of 0.075-0.16 mm. Spraying a 6% calcium chloride solution onto surfaces of the inorganic solid waste-microbial composite curing agent A and the inorganic solid waste-microbial composite curing agent B to keep the surfaces wet, spraying at intervals of 8 hours once, and repeating 2 times.

Mixing 25% inorganic solid waste-microbial composite curing agent A, 10% inorganic solid waste-microbial composite curing agent B, and 65% sludge evenly, then introducing 5% by mass of $CO_2$ to conduct carbonisation during mixing; after carbonisation for 48 hours, curing the mixture in the standard curing box under the temperature of 20° C. and the humidity greater than 95% to the age of 28 d, so as to obtain solidified silt soil.

Embodiment 2

A method of preparing the inorganic solid waste-microbial composite curing agent includes the following steps:

S1. Preparation of Solid Waste Porous Material

Performing granulation on steel slag, active magnesium oxide, recycled powder, stearic acid, borax through dry rolling extrusion and compression using a granulator, which can effectively maintain the mineral activity of the steel slag and recycled powder. The heating device is turned on to raise the temperature of the material to 1120° C., and the solid waste porous material with a diameter of 2-3 mm is obtained through cutting, granulating, and screening processes;

Solid waste porous materials, calculated by weight, include: 30 parts of the steel slag, 30 parts of the active magnesium oxide, 20 parts of the recycled powder, 7 parts of the stearic acid, and 2 part of the borax.

S2. Modification of the Solid Waste Porous Material

Taking zinc nitrate hexahydrate and ferrous chloride to add into a mixed solution of methanol and deionized water, then adding the solid waste porous material, stirring for 3 h, then washing and drying to obtain a modified solid waste porous material;

The mass ratio of the zinc nitrate hexahydrate, the ferrous chloride, the methanol, the deionized water, and the solid waste porous material is 12:3:200:300:500.

S3. Cultivation of Carbonic Anhydrase Bacteria and *Bacillus subtilis* with High pH Resistance Inoculating carbonic anhydrase bacteria and *Bacillus subtilis* into culture dishes with a pH value of 12, screening and domesticating them to obtain carbonic anhydrase bacteria and *Bacillus subtilis* that can tolerate pH 10;

S4. Preparation of the Composite Bacterial Agent of Carbonic Anhydrase Bacteria and *Bacillus subtilis*

Performing centrifugation to obtain carbonic anhydrase bacterial sludge and *Bacillus subtilis* bacterial sludge respectively, taking 1 weight part of the carbonic anhydrase bacterial sludge and adding it into 200 weight parts of sodium alginate saturated solution, then performing centrifugation after stirring to obtain carbonic anhydrase bacteria microcapsules; taking 1 weight part of the *Bacillus subtilis* bacterial sludge and adding it into 200 weight parts of sodium alginate saturated solution, then performing centrifugation after stirring to obtain *Bacillus subtilis* microcapsules;

Then mixing 0.3 weight parts of the carbonic anhydrase bacteria microcapsules and 0.3 weight parts of the *Bacillus subtilis* microcapsules uniformly, and then drying to obtain the composite microbial agent;

S5. Preparation of the Inorganic Solid Waste-Microbial Composite Curing Agent

Adding 0.6 weight parts of the composite microbial agent and 6 weight parts of the soluble calcium salt into 50 weight parts of deionized water to obtain a mixed solution, then impregnating the modified solid waste porous material obtained in S2 into the mixed solution for 20 min under vacuum negative pressure, then drying to obtain the inorganic solid waste-microbial composite curing agent.

Crushing and sieving the inorganic solid waste-microbial composite curing agent to obtain an inorganic solid waste-microbial composite curing agent A with a particle size of 0.17-3 mm and an inorganic solid waste-microbial composite curing agent B with a particle size of 0.075-0.16 mm. Spraying a 6% calcium chloride solution onto surfaces of the inorganic solid waste-microbial composite curing agent A and the inorganic solid waste-microbial composite curing agent B to keep the surfaces wet, spraying at intervals of 8 hours once, and repeating 2 times.

Mixing 25% inorganic solid waste-microbial composite curing agent A, 10% inorganic solid waste-microbial composite curing agent B, and 65% sludge evenly, then introducing 5% by mass of $CO_2$ to conduct carbonisation during mixing; after carbonisation for 48 hours, curing the mixture in the standard curing box under the temperature of 20° C. and the humidity greater than 95% to the age of 28 d, so as to obtain solidified silt soil.

Embodiment 3

A method of preparing the inorganic solid waste-microbial composite curing agent includes the following steps:

S1. Preparation of Solid Waste Porous Material

Performing granulation on steel slag, active magnesium oxide, recycled powder, stearic acid, borax through dry rolling extrusion and compression using a granulator, which can effectively maintain the mineral activity of the steel slag and recycled powder. The heating device is turned on to raise the temperature of the material to 1120° C., and the solid waste porous material with a diameter of 2-3 mm is obtained through cutting, granulating, and screening processes;

Solid waste porous materials, calculated by weight, include: 20 parts of the steel slag, 40 parts of the active magnesium oxide, 20 parts of the recycled powder, 8 parts of the stearic acid, 3 part of the borax, and 4 parts of soluble calcium salt.

S2. Modification of the Solid Waste Porous Material

Taking zinc nitrate hexahydrate and ferrous chloride to add into a mixed solution of methanol and deionized water, then adding the solid waste porous material, stirring for 3 h, then washing and drying to obtain a modified solid waste porous material;

The mass ratio of the zinc nitrate hexahydrate, the ferrous chloride, the methanol, the deionized water, and the solid waste porous material is 12:3:200:300:500.

S3. Cultivation of Carbonic Anhydrase Bacteria and *Bacillus subtilis* with High pH Resistance Inoculating carbonic anhydrase bacteria and *Bacillus subtilis* into culture dishes with a pH value of 12 respectively, screening and domesticating them to obtain carbonic anhydrase bacteria and *Bacillus subtilis* that can tolerate pH 10;

S4. Preparation of the Composite Bacterial Agent of Carbonic Anhydrase Bacteria and *Bacillus subtilis*

Performing centrifugation to obtain carbonic anhydrase bacterial sludge and *Bacillus subtilis* bacterial sludge respectively, taking 1 weight part of the carbonic anhydrase bacterial sludge and adding it into 200 weight parts of sodium alginate saturated solution, then performing centrifugation after stirring to obtain carbonic anhydrase bacteria microcapsules; taking 1 weight part of the *Bacillus subtilis* bacterial sludge and adding it into 200 weight parts of sodium alginate saturated solution, then performing centrifugation after stirring to obtain *Bacillus subtilis* microcapsules;

Then mixing 0.4 weight parts of the carbonic anhydrase bacteria microcapsules and 0.4 weight parts of the *Bacillus subtilis* microcapsules uniformly, and then drying to obtain the composite microbial agent;

S5. Preparation of the Inorganic Solid Waste-Microbial Composite Curing Agent

Adding 0.8 weight parts of the composite microbial agent and 6 weight parts of the soluble calcium salt into 50 weight parts of deionized water to obtain a mixed solution, then impregnating the modified solid waste porous material obtained in S2 into the mixed solution for 20 min under vacuum negative pressure, then drying to obtain the inorganic solid waste-microbial composite curing agent.

Crushing and sieving the inorganic solid waste-microbial composite curing agent to obtain an inorganic solid waste-microbial composite curing agent A with a particle size of 0.17-3 mm and an inorganic solid waste-microbial composite curing agent B with a particle size of 0.075-0.16 mm. Spraying a 6% calcium chloride solution onto surfaces of the inorganic solid waste-microbial composite curing agent A and the inorganic solid waste-microbial composite curing agent B to keep the surfaces wet, spraying at intervals of 8 hours once, and repeating 2 times.

Mixing 25% inorganic solid waste-microbial composite curing agent A, 10% inorganic solid waste-microbial composite curing agent B, and 65% sludge evenly, then introducing 5% by mass of $CO_2$ to conduct carbonisation during mixing; after carbonisation for 48 hours, curing the mixture in the standard curing box under the temperature of 20° C. and the humidity greater than 95% to the age of 28 d, so as to obtain solidified silt soil.

Comparative Example 1

The difference between Comparative example 1 and Embodiment 1 is that the solid waste porous material prepared by taking 20 parts of steel slag, 30 parts of active magnesium oxide, and 30 parts of recycled powder is used as a sludge curing agent, without loading carbonic anhydrase bacteria and *Bacillus subtilis* microcapsules.

Comparative Example 2

The difference between Comparative example 2 and Embodiment 1 is that 0.2 parts of carbonic anhydrase bacteria microcapsules and 0.2 parts of *Bacillus subtilis* microcapsules are taken as a sludge curing agent, without adding steel slag, active magnesium oxide, recycled powder, stearic acid, and borax.

Comparative Example 3

The difference between Comparative example 3 and Embodiment 1 is that $CO_2$ is not introduced during the curing process of the sludge.

Experiment

The solidified sludge prepared from Embodiment 1 to Embodiment 3 and from Comparative example 1 to Comparative example 3 were subjected to unconfined compressive strength test, and the data obtained are shown in the table below:

| Sorts | 3 d | 7 d | 28 d |
|---|---|---|---|
| Embodiment 1 | 0.4 | 1.6 | 1.9 |
| Embodiment 2 | 0.6 | 1.7 | 2.0 |
| Embodiment 3 | 0.9 | 1.9 | 2.1 |
| Comparative example 1 | 0.3 | 0.7 | 1.0 |
| Comparative example 2 | 0.1 | 0.4 | 0.7 |
| Comparative example 3 | 0.3 | 1.4 | 1.5 |

Conclusion: From the table, it can be seen that the unconfined compressive strengths of the solidified sludge prepared in Embodiments 1-3 are much higher than that of the solidified sludge prepared in Comparative examples 1-3 at 3 d, 7 d, and 28 d, and the unconfined compressive strength at 7 d is higher than 1.5 MPa. This indicates that the curing effect of the inorganic solid waste-microbial composite curing agent is significantly better than that of a single inorganic curing agent and microbial curing agent, and the sludge curing process absorbs a large amount of $CO_2$, helping to achieve the dual goals of carbon peak and carbon neutrality.

It can be seen that the inorganic solid waste-microbial composite curing agent and its preparation method and application provided by the present disclosure fully utilize the carbonization of inorganic solid waste and microbial mineralization such as steel slag, active magnesium oxide, and recycled powder to solidify sludge in coordination, with fast solidification speed and high soil strength. The present disclosure turns solid waste and sludge into treasure, and seals and utilizes $CO_2$ during the curing process, which has advantages such as excellent economy and environmental friendliness, and broad application prospects.

Finally, it should be noted that the above is only part of preferred embodiments of the present disclosure and is not intended to limit it. Although the present disclosure has been described in detail with reference to the aforementioned embodiments, it is still possible for those skilled in the art to modify the technical solutions recorded in the aforementioned embodiments or to equivalently replace some of their technical features. Any modifications, equivalent substitutions, improvements, etc. made within the spirit and principles of the present disclosure shall be included within the scope of the present disclosure.

What is claimed is:

1. An inorganic solid waste-microbial composite curing agent, characterized in that: the inorganic solid waste-microbial composite curing agent comprises following components in parts by weight: 20-30 parts of steel slag, 30-40 parts of activated magnesium oxide, 20-30 parts of recycled powder, 5-10 parts of foaming agent, 1-5 parts of foam stabilizer, 0.4-0.8 parts of composite microbial agent, 2-8 parts of soluble calcium salt; the composite microbial agent comprises carbonic anhydrase bacteria microcapsules and *Bacillus subtilis* microcapsules, produced by a method comprising the following steps:

S1. preparation of solid waste porous material:

mixing the steel slag, the activated magnesium oxide, the recycled powder, the foaming agent, the foam stabilizer and performing extrusion granulation, heating the material to 1110-1120° C., then cutting, granulating, and sieving to obtain a solid waste porous material;

S2. modification of the solid waste porous material:

taking zinc nitrate hexahydrate and ferrous chloride to add into a mixed solution of methanol and deionized water, then adding the solid waste porous material, stirring for 2-3 h, then washing and drying to obtain a modified solid waste porous material;

S3. cultivation of carbonic anhydrase bacteria and *Bacillus subtilis* with high pH resistance:

conducting domestication on carbonic anhydrase bacteria and *Bacillus subtilis* separately, while adjusting a pH of a culture solution to 10-12, and screening the carbonic anhydrase bacteria and the *Bacillus subtilis* to obtain the carbonic anhydrase bacteria and *Bacillus subtilis* that are able to tolerate a pH of 10;

S4. preparation of the composite bacterial agent of carbonic anhydrase bacteria and *Bacillus subtilis:* performing centrifugation to obtain carbonic anhydrase bacterial sludge and *Bacillus subtilis* bacterial sludge respectively, then separately adding sodium alginate saturated solution, then performing centrifugation after stirring to obtain carbonic anhydrase bacteria microcapsules and *Bacillus subtilis* microcapsules, respectively, then mixing the carbonic anhydrase bacteria microcapsules and the *Bacillus subtilis* microcapsules uniformly, and then drying to obtain the composite microbial agent:

S5. preparation of the inorganic solid waste-microbial composite curing agent adding the composite microbial agent and the soluble calcium salt into deionized water to obtain a mixed solution, then impregnating the modified solid waste porous material in the mixed solution for 15-20 min under vacuum negative pressure, then drying to obtain the inorganic solid waste-microbial composite curing agent.

2. The inorganic solid waste-microbial composite curing agent according to claim 1, wherein the recycled powder is construction waste powder; the foaming agent is stearic acid; and the foam stabilizer is borax.

3. The inorganic solid waste-microbial composite curing agent according to claim 1, wherein the steel slag, the activated magnesium oxide, the recycled powder, the foaming agent, the foam stabilizer are sieved through a 100 mesh sieve.

4. The inorganic solid waste-microbial composite curing agent according to claim 1, wherein the soluble calcium salt is any one of calcium chloride, calcium bromide, calcium nitrate, and calcium bicarbonate.

5. The inorganic solid waste-microbial composite curing agent A according to claim 1, wherein a mass ratio of the carbonic anhydrase bacteria microcapsules: *Bacillus subtilis* microcapsules is (1-2):(1-2).

6. A method of utilizing the inorganic solid waste-microbial composite curing agent according to claim 1, comprising the following steps:

step 1: crushing and sieving the inorganic solid waste-microbial composite curing agent to obtain an inorganic solid waste-microbial composite curing agent A with a particle size of 0.17-3 mm and an inorganic solid waste-microbial composite curing agent B with a particle size of 0.075-0.16 mm;

step 2: spraying a 5-8% calcium chloride solution onto surfaces of the inorganic solid waste-microbial composite curing agent A and the inorganic solid waste-microbial composite curing agent B to keep the surfaces wet, spraying at intervals of 6-8 hours once, and repeating 2-3 times;

step 3: mixing and stirring the inorganic solid waste-microbial composite curing agent B and the sludge for 5-10 min;

step 4: adding the inorganic solid waste-microbial composite curing agent A, and continuously stirring for 5-10 min;

step 5: moulding a specimen after standing for 10-12 h, placing the specimen into a sealed space, then introducing $CO_2$ to conduct carbonisation, demoulding the specimen after 48 hours, and then curing for the specimen to obtain an ecological porous building material.

7. The method according to claim 6, wherein in the step 3, the mass ratio of the inorganic solid waste-microbial composite curing agent B and the sludge is 1:(5-10), and the moisture content of the sludge is 40%-60%;

in the step 4, the inorganic solid waste-microbial composite curing agent A accounts for 30%-40% of the mass of the sludge;

in the step 5, the curing temperature is 18-25° C., and the humidity is 95-98 percent.

* * * * *